US008287502B2

(12) United States Patent
Blumenthal et al.

(10) Patent No.: US 8,287,502 B2
(45) Date of Patent: Oct. 16, 2012

(54) GASTROSTOMY BUTTON ACCESSORY MOUNTING PLATFORM

(76) Inventors: Jeffrey Blumenthal, Sandy Springs, GA (US); Dan Nichols, Tampa, FL (US)

( * ) Notice: Subject to any disclaimer, the term of this patent is extended or adjusted under 35 U.S.C. 154(b) by 0 days.

(21) Appl. No.: 12/761,226

(22) Filed: Apr. 15, 2010

(65) Prior Publication Data

US 2010/0268172 A1 Oct. 21, 2010

Related U.S. Application Data

(60) Provisional application No. 61/212,822, filed on Apr. 16, 2009.

(51) Int. Cl.
*A61M 5/00* (2006.01)

(52) U.S. Cl. ......... 604/263; 604/19; 604/48; 604/93.01; 604/174

(58) Field of Classification Search .................. 604/179, 604/247, 263, 19, 48, 93.01
See application file for complete search history.

(56) References Cited

U.S. PATENT DOCUMENTS

| | | | | |
|---|---|---|---|---|
| 4,944,732 | A * | 7/1990 | Russo | 604/247 |
| 5,072,843 | A | 12/1991 | James | |
| 5,549,657 | A * | 8/1996 | Stern et al. | 604/537 |
| 5,690,096 | A | 11/1997 | Burch | |
| 6,438,758 | B1 | 8/2002 | Burkard et al. | |
| 6,634,919 | B2 | 10/2003 | Gordon et al. | |
| 6,789,542 | B1 | 9/2004 | Bischoff | |
| 2005/0090783 | A1 | 4/2005 | Sibbitt, Jr. | |
| 2005/0113740 | A1 | 5/2005 | Oberhofer | |
| 2005/0209567 | A1 | 9/2005 | Sibbitt, Jr. | |
| 2006/0084923 | A1 * | 4/2006 | Lotartaro | 604/179 |
| 2009/0254039 | A1 * | 10/2009 | O'Brien et al. | 604/174 |

* cited by examiner

*Primary Examiner* — Kevin C Sirmons
*Assistant Examiner* — Brandy C Scott
(74) *Attorney, Agent, or Firm* — Hill, Kerschier & Wharton, LLP; Gregory T. Ouroda

(57) ABSTRACT

A accessory mounting system for use with gastrostomy buttons is herein described. The system consists of an accessory mounting platform and a cap that is able to be manually attached and detached from the accessory mounting platform. The accessory mounting platform can be integrally mounted to either the keeper strap or the head of the gastrostomy button, or it can be attached to the keeper strap of an existing gastrostomy button using a clip integrally attached to its underside.

3 Claims, 7 Drawing Sheets

Bard® G-Button

Mic-Key® G-button

GASTROSTOMY BUTTON ACCESSORY MOUNTING PLATFORM

CROSS REFERENCE TO RELATED APPLICATIONS

This application claims priority to provisional application Ser. No. 61/212,822 filed Apr. 16, 2009.

BACKGROUND OF THE INVENTION

Gastrostomy buttons ("G-buttons") are used by physicians in pediatric and adult patients with feeding/swallowing disorders. Patients with feeding difficulties are at risk for malnutrition, dehydration, and aspiration. Many patients are premature infants, infants with congenital heart disease, and young children who are neurologically impaired due to brain tumors, cerebral palsy, or traumatic brain injury. Children and adults receiving chemotherapy comprise another large subgroup of patients requiring nutritional support through supplemental feeding tubes such as a G-buttons. Many gastrostomy dependent patients are unable to communicate depending entirely on their health care providers to administer the appropriate formula/feeding regimen. Hospitalized patients often have their feeding regimens changed on a regular basis.

Most feeding tubes are placed endoscopically as percutaneous endoscopic gastrostomy (PEG) tubes. Gastrostomy tubes are typically replaced by G-buttons after 2-3 months' time. Patients and families prefer G-buttons to G tubes because G-buttons are small flat skin-level devices that are less obtrusive and more cosmetically appealing than G tubes. However, G-buttons still remain unsightly because of their unnatural appearance against a patient's abdominal skin. G-buttons are also preferred over G tubes because they easily connect/disconnect from extension tubing through which nourishment is provided. All G-buttons manufactured are presently non-decorative being made from clear or white plastics that are easily visualized against the patient's abdominal wall.

There are two types of gastrostomy buttons. The Bard® G-button shown in FIG. 1 has a mushroom-shaped dome that sits in the stomach lumen. The mushroom shape serves to anchor the tube in the stomach lumen and prevents the tube penetrating the abdominal wall from inadvertently slipping out of the abdomen. These buttons require a special stylet for placement and removal.

The Mic-Key® G-button manufactured by Kimberly-Clark Corp. shown in FIG. 2 has a water balloon in place of the mushroom shaped dome that is inflated/deflated for insertion and removal. All G-buttons incorporate a check valve assembly that allows liquid nourishment to flow into the patient's stomach, while preventing gastric contents from leaking outward. G-buttons are often placed on a semi-permanent basis; they must be changed out periodically as patients outgrow their button sizes. Balloons also deteriorate with time and pop requiring complete button replacement. Many patients will require a lifetime of supplemental G-button feedings.

There are a number of significant problems associated with G-button placement. Chief among these is the negative psychological association with placement of a permanent feeding tube. Placement of a G-button is a last resort, when all other therapies and techniques to provide nutritional support have failed. Thus, for the families of patients, placement of a G-button is often tantamount to admitting defeat. Placement of a G-button is commonly associated with a lack of progress with therapeutic interventions to improve oral feeding skills. For the patient and his/her family, placement of a permanent feeding tube therefore is symbolic of the patient's chronic underlying medical/neurological condition and confirms the permanence of the condition. Adults requiring permanent feeding tubes have similar negative psychological reactions to G-buttons for many of the same reasons. Adults, adolescents, and children are typically conscious of the unsightly appearance of an exposed G-button on the abdomen. Because of this, patients may delay placement of a G-button. This can result in further malnutrition, which ultimately exacerbates their underlying medical condition.

BRIEF SUMMARY OF THE INVENTION

The current invention seeks to ameliorate the negative association and distress associated with placement of a G-button by providing a means to alter the intimidating appearance of the gastrostomy button, and to display feeding instructions. The current invention consists of an accessory mounting platform to which detachable caps may be fastened. This platform is integral with a keeper strap that is attached to the G-button or is attached via a clip on the underside of the mounting platform. The mounting platform having a hole accommodating the insertion of a feeding tube can also be attached directly to the head of the G-button, without the use of a keeper strap. The platform is typically wider than the accessory mounting platform so that it covers the visible face of the G-button when viewed from a distance.

The accessory mounting platform allows detachable caps of various designs to be attached altering the outward appearance of the device. The detachable caps can be changed daily by the patient to alter the outer appearance of the gastrostomy button. Caps may have a variety of colorful designs/logos imprinted and or applied. Designs can include cartoon characters, sports logos, symbols, flowers, or animals, as shown in FIG. 6. These decorative attachments are not limited to designs for children; adults fitted with G-buttons will also benefit from the invention. For adults, decorative attachments will include sports team logos, symbols, trademarks, or even precious stones embedded in the cap, as shown in FIGS. 7 and 8.

Alternatively, the base can have a permanent design on its outer surface or provide a surface to display a sticker outlining the patient's feeding regimen as shown in FIGS. 5 and 9. Patients requiring G tubes are often cared for by providers outside the home such as school nurses, hospital nurses, or day care providers. Stickers attached to the accessory mounting platform or to the removable cap will state the patient's current feeding regimen, offering a safeguard from feeding errors. Stickers placed on the top surface of the accessory mounting platform may also be in lieu of a decorative cap.

The embodiments described herein enhance patients' medical condition by removing the negative psychological associations of G-buttons by making them fun, decorative and less "medical" in appearance. This in turn may have the effect of allowing nutritional support to be delivered earlier in an illness. One particular embodiment described herein also serves to improve the quality of patient care by displaying the patient's most current, specific feeding orders, reducing errors in feeding instructions.

DETAILED DESCRIPTION OF THE INVENTION

Figure 1:
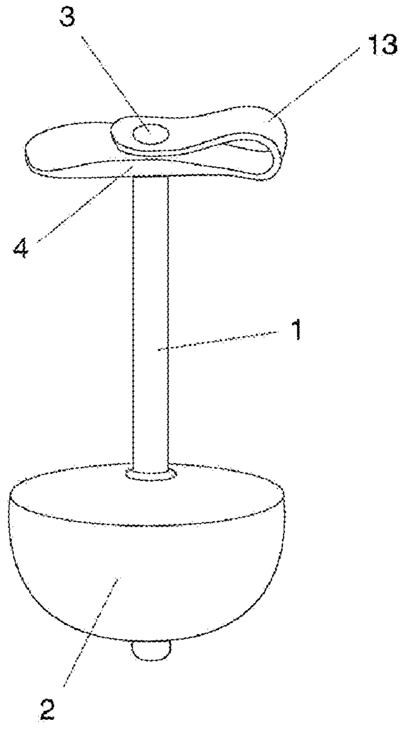
FIG. 1 shows a conventional Bard® type G-button

There are two primary types of gastrostomy buttons ("G-buttons") in use today. The first type, (called the Bard® Button) produced by Bard Access Systems and shown in FIG. 1 has a hollow stem 1 that is inserted through the abdominal wall into the stomach and is held in place therein by a semi-rigid, mushroom-shaped bolster 2. Feeding port 3, (shown covered in FIG. 1) lies on the exterior of the patient's left upper abdomen. It allows extension tubing to be attached to the G-button, which in turn allows nutritional support to be delivered directly into the patient's stomach through stem 1. As shown in FIG. 1, the Bard® Button has a thin, plain, non-decorative plug on a keeper strap 13 which seals the opening to the stem in the head 4 of the G-button when it is not in use.

Figure 2:
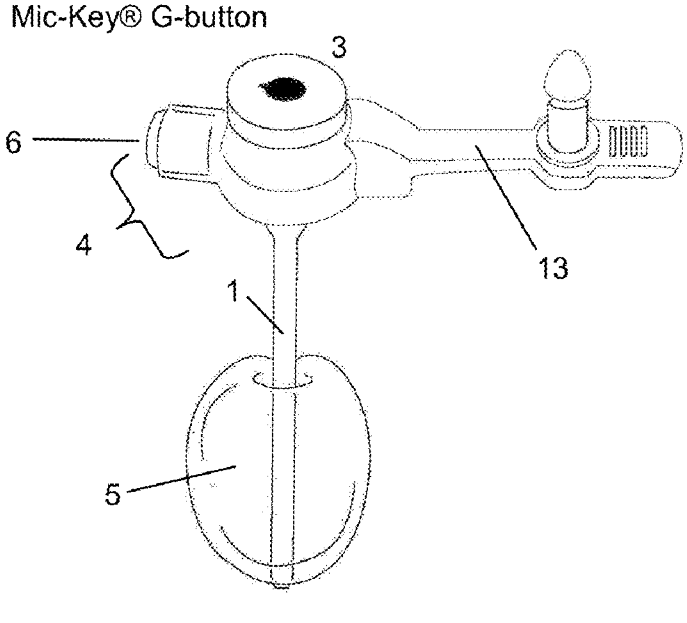
FIG. 2 shows a conventional Mic-Key® type G-button.

The Mic-Key® gastrostomy button manufactured by Kimberly-Clark Corp. and shown in FIG. 2 features an inflatable water balloon 5 at the end of stem 4 that is inserted into the patient's stomach. The water balloon acts as a bolster to keep the stem 1 from sliding out of the hole in the patient's abdomen. Two ports are positioned on the head at the opposite end of the stem from the water balloon. These ports lie on the exterior of the patient's left upper abdomen. An inflation port 6 is used to inflate the water balloon. In current Mic-Key® devices, the inflation port is a relatively large conical structure that allows standard syringes to be used to inflate the water balloon. As with the Bard® G-button, feeding port 3 is used to connect the extension tubing to the G-button, allowing nutritional support to be delivered directly to the patient's stomach.

Figure 3:
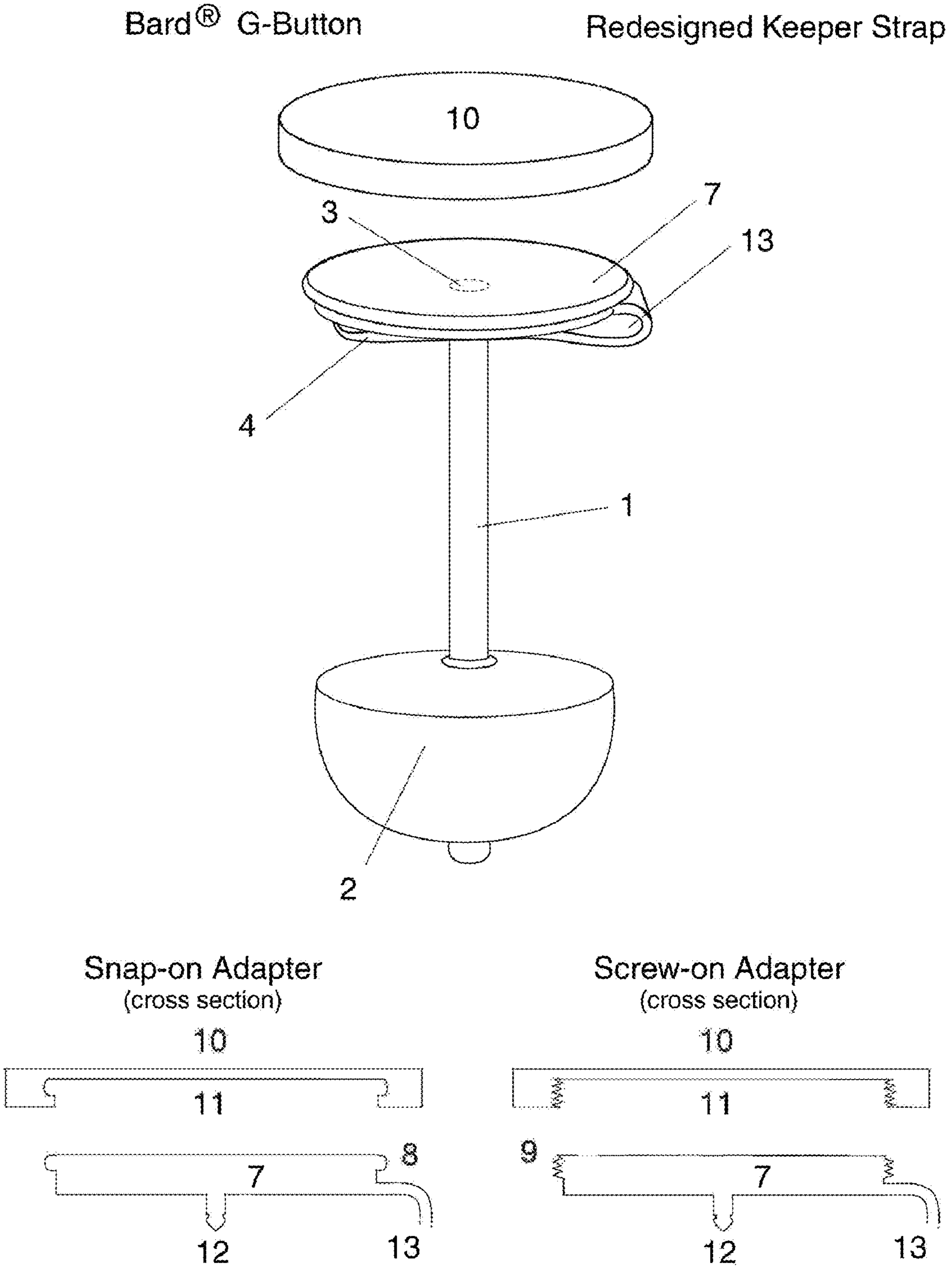
FIG. 3 shows one embodiment of the accessory mounting platform.

Turning now to the embodiments of the invention, a removable metal or plastic cap 10 shown in FIG. 3 bears an ornamental design or pattern that can be imprinted, engraved, embossed, molded, or affixed directly into the cap. In the preferred embodiments of the invention, this cap is snapped or screwed onto accessory mounting platform 7 that in certain embodiments is used in lieu of a conventional plug to seal feeding port 3 of the G-button. Cap 10 is removable so that the patient using a G-button can interchange different removable cap designs as desired.

Accessory mounting platform 7 is made of molded plastic and should be stiff enough to hold the cap firmly, yet flexible enough to allow the cap to be easily removed. As will be readily appreciated, variations in the type of materials used for both the cap 10 and the accessory mounting platform 7 are possible. Although plastic is used in the preferred embodiments of the invention, use of other materials of suitable durometer such as silicone can be used for both the cap and accessory mounting platform.

A first embodiment of the invention is displayed in FIG. 3. In this embodiment accessory mounting platform 7 is attached to the G-button using keeper strap 13 and plug 12 is molded integrally with the accessory mounting platform. The accessory mounting platform 7 allows the cap to be securely fastened yet easily removed. The upper side of accessory mounting platform 7 contains a male end 8, 9 which engages the bottom of removable cap 10 containing female end 11. The lower side of accessory mounting platform 7 is a plug 12 which seals the opening of feeding port 3.

It will be noted by one skilled in the art that that accessory mounting platform 7 can have a male end with raised threads 9, as shown in FIG. 3 (bottom right) which engage complimentary threads in the female end 11 of decorative cap 10, allowing the cap to be screwed securely onto the accessory mounting platform. Accessory mounting platform 7 can also have the cap 10 and accessory mounting platform 8 made so that the former snaps onto the latter, as shown in FIG. 3. This is accomplished by having complementary convex circumferential ridges and concave indentations in the male and female ends of the accessory mounting platform and cap, respectively. The complementary convex ridges and concave indentations fit together when the cap is affixed to the base. Of course, the position of the male and female ends may also be reversed from what is described above; that is, the male end may appear on the cap and the female end on the accessory mounting platform.

Figure 4:
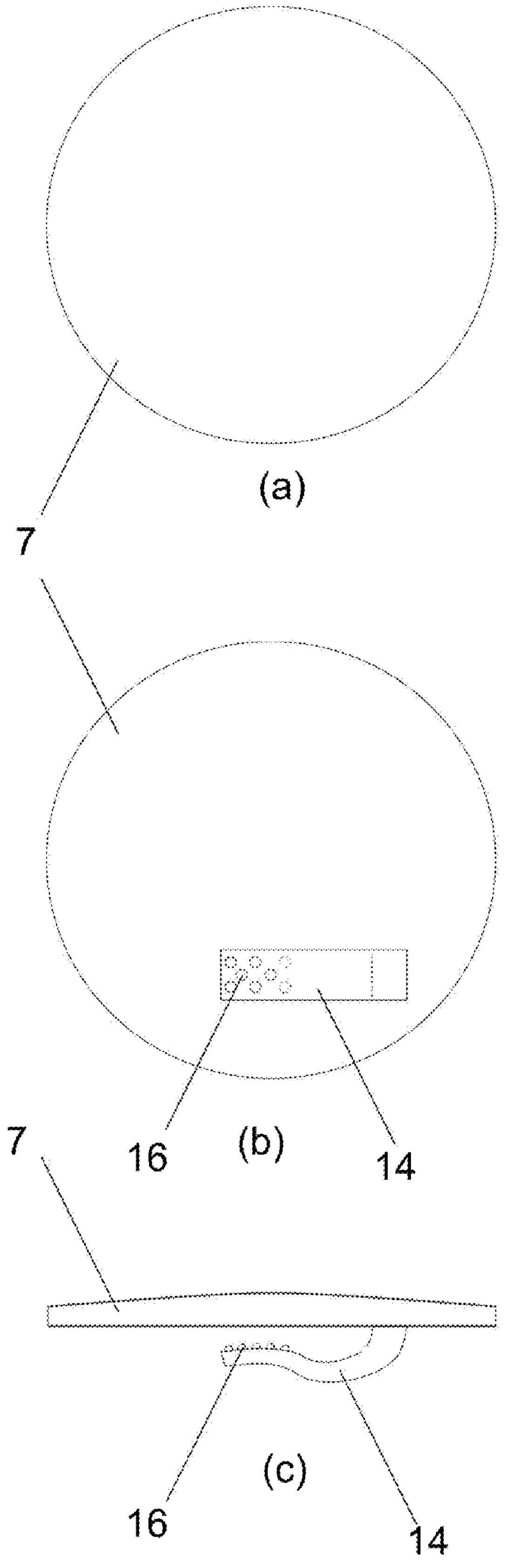
FIG. 4 shows a detailed view of one embodiment of the accessory mounting platform.
Figure 5:
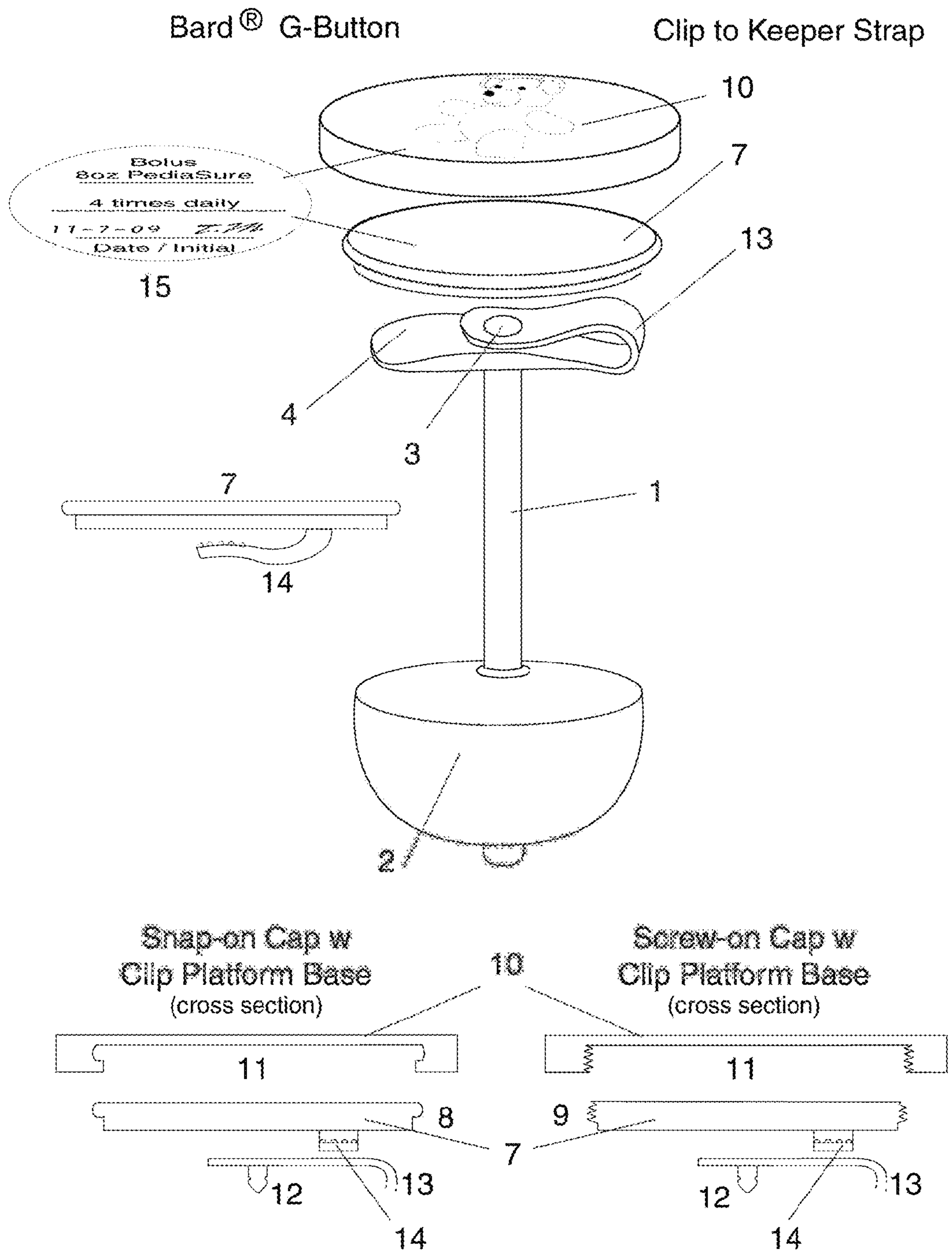
FIG. 5 shows one embodiment of the accessory mounting platform.
Figure 9:
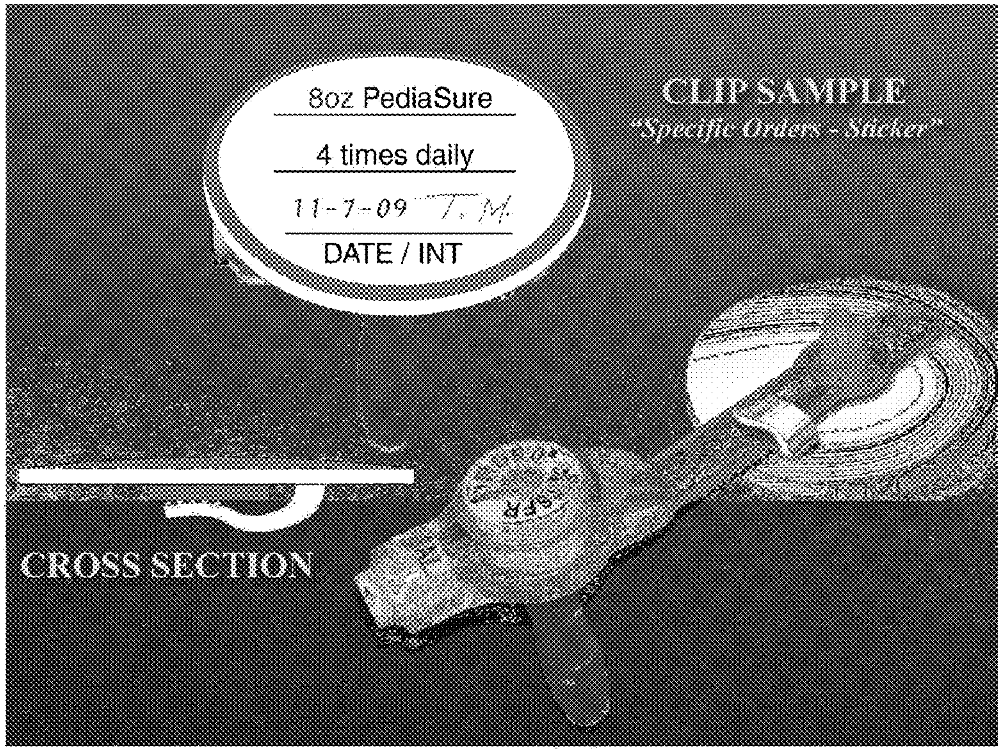
FIG. 9 is an illustration of certain ornamental features applied to the detachable cap.

In another embodiment of the invention, the accessory mounting platform 7 is attached to keeper strap 13 using a clip 14, as shown in FIGS. 4(*b*) and 4(*c*). Clip 14 may additionally contain raised protrusions 16 to enable more secure fastening of the accessory mounting platform to the keeper strap. The advantage of this embodiment is that it can be used with currently-existing G-buttons; that is, this embodiment does not require specially-manufactured G-buttons with accessory mounting platform 7 integral with keeper strap 13. FIG. 5 shows this embodiment being used with a legacy Bard® G-button. FIGS. 5 and 9 also show that the accessory mounting platform 7 may have a sticker 15 placed thereon, under cap 10. Sticker 15 contains feeding instructions or other patient data and is readily viewable by the patient or caregiver by simply removing cap 10. This reduces errors in feeding instructions.

Figure 6:
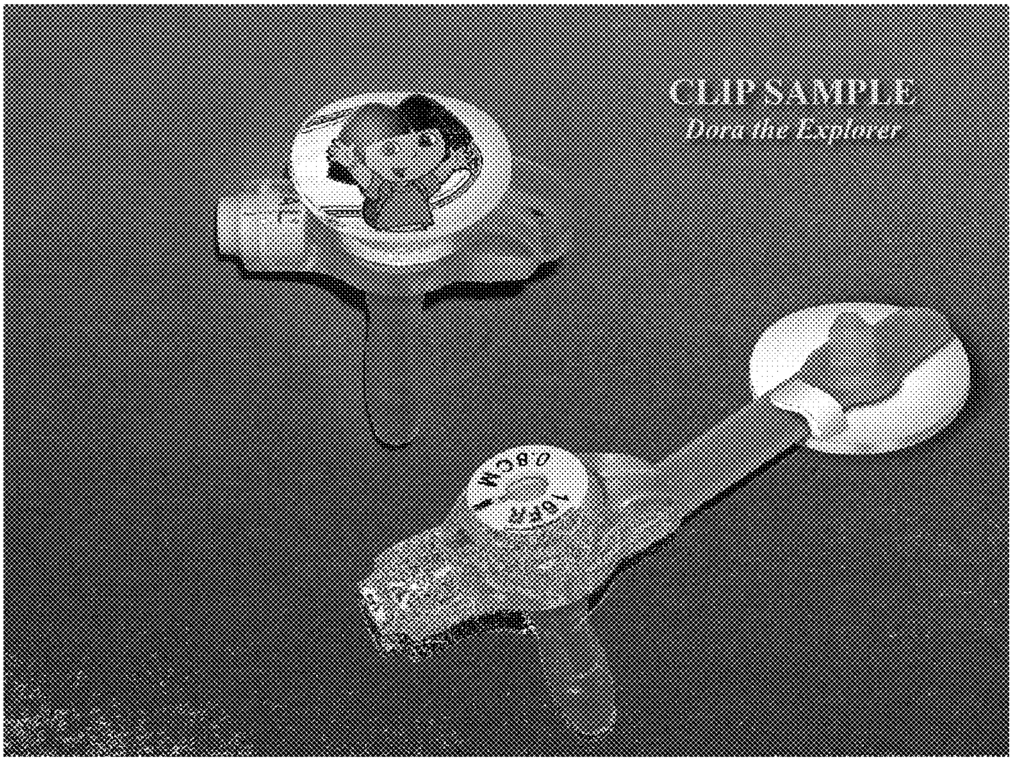
FIG. 6 is an illustration of certain ornamental features applied to the detachable cap.
Figure 7:
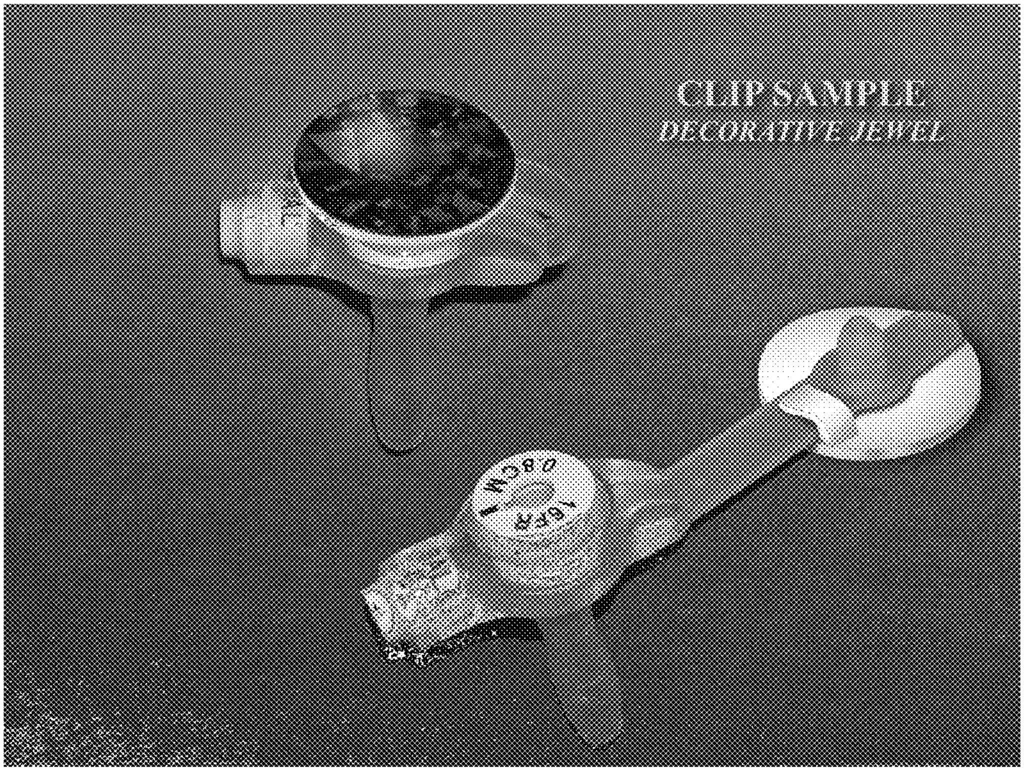
FIG. 7 is an illustration of certain ornamental features applied to the detachable cap.
Figure 8:
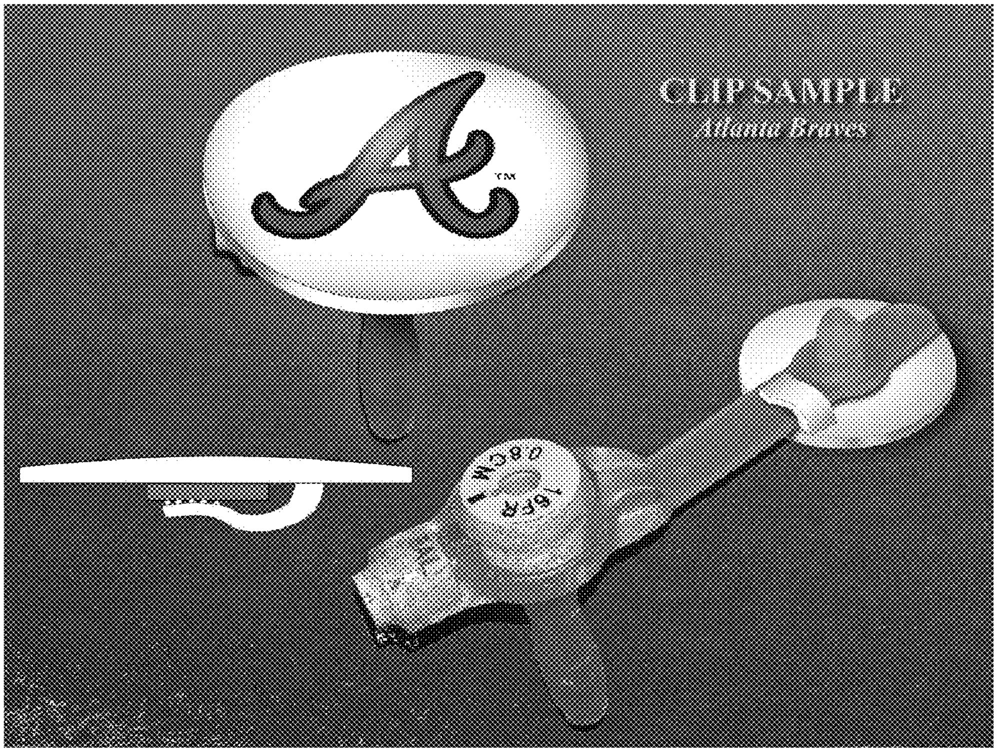
FIG. 8 is an illustration of certain ornamental features applied to the detachable cap.

As mentioned previously, removable cap 10 can be made of metal or plastic and may bear an infinite variety of decorative enhancements, examples of which are shown in FIGS. 6, 7, and 8.

Figure 10:
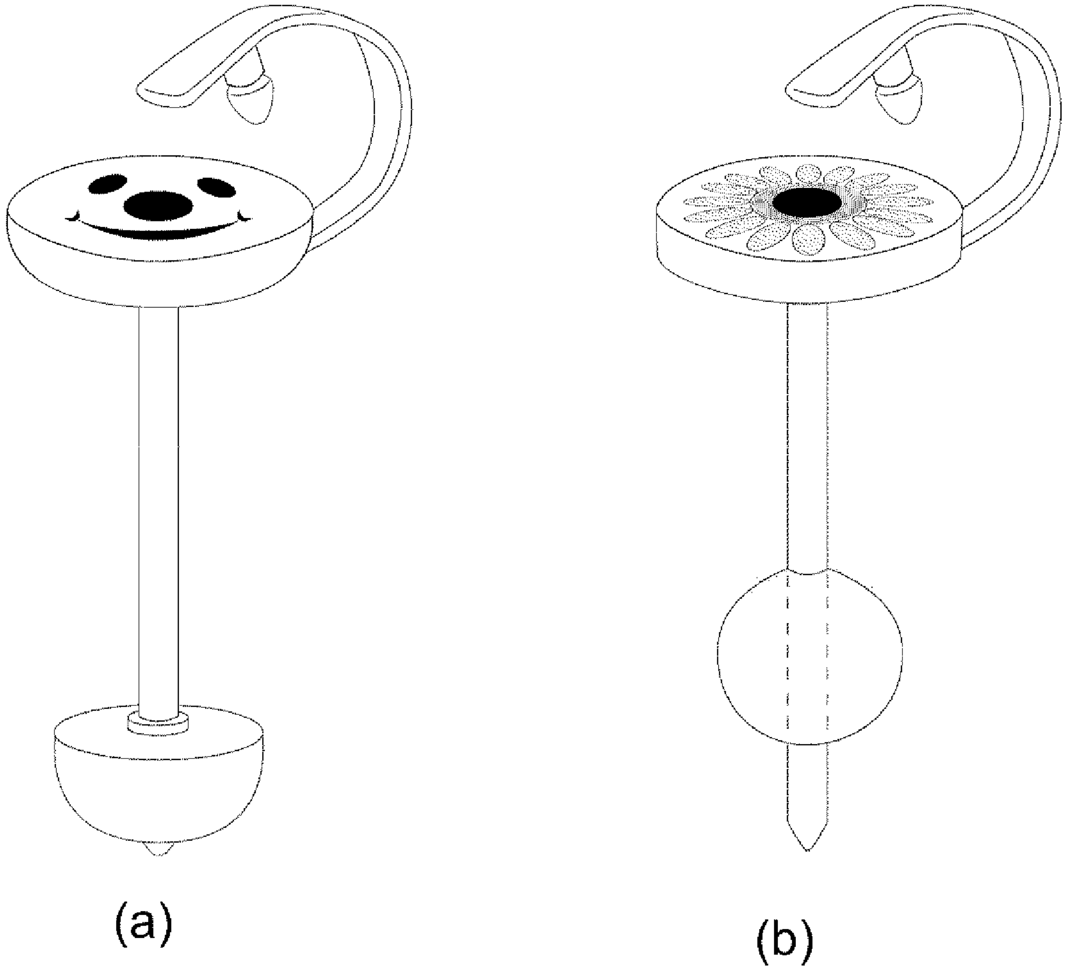
FIG. 10 shows one embodiment of the removable cap and accessory mounting platform.

In yet another embodiment of the invention shown in FIGS. 10(*a*) (showing the invention in use with a Bard® G-button) and 10(*b*) (showing the invention embodiment in use with a Mic-Key® G-button), accessory mounting platform 7 is mounted integrally to head 4 of the G-button. Removable cap 10 would attach to the accessory mounting platform 7 as described above. In this embodiment, it is of course necessary for both accessory mounting platform 7 and removable cap 10 to have a hole to accommodate the attachment of a feeding tube. A plug on the end of keeper strap 13 would also be necessary to seal the port when not in use. The advantage of this particular embodiment is that the logo on the cap would be visible when the feeding port 3 is in use, since the port is embedded in the center of the cap. However, the cap would be less attractive when the feeding port 3 is not in use, since the plug and strap will be clearly visible.

Finally, it should also be noted that it is desirable to change the color of the material used to produce the G-button itself from the opaque gray that is typically used, to another color in order to reduce the intimidating "medical" appearance of the device.

What is claimed is:

1. An accessory mounting system, comprising:

a gastrostomy button comprising, a head having a feeding port therein and, a keeper strap having a first end and a second end, said first end integrally attached to said head;

a mounting platform integrally attached to said keeper strap's second end, said mounting platform having an upper side and a lower side, said upper side of said mounting platform having male attachment means defined by a raised cylindrical structure, said lower side of said mounting platform having a plug for said feeding port;

a substantially flat interchangeable cap having an upper side and a lower side, said lower side of said cap having female attachment means defined by a cylindrical cavity complementary to said mounting platform's male attachment means;

wherein said male attachment means engages said female attachment means allowing said cap to be removably attached to said mounting platform.

2. An accessory mounting system, comprising:

a gastrostomy button comprising, a head with a feeding port therein, and a keeper strap having a first and a second end, said first end being attached to said head and said second end having a plug for said feeding port;

a mounting platform having an upper side and a lower side; said upper side having male attachment means; said lower side having a clip allowing said mounting platform to be removably attached to said keeper strap; and a substantially flat interchangeable cap having an upper side and a lower side, said lower side having female attachment means complementary to said male attachment means of said mounting platform;

wherein said male and said female attachment means permit said cap to be removably attached to said mounting platform.

3. An accessory mounting system, consisting of: a gastrostomy button comprising, a head having a feeding port therein and, a keeper strap having a first end and a second end, said first end integrally attached to said head; a mounting platform having an upper side and a lower side, said upper side having male attachment means, said lower side having a plug for said feeding port, said mounting platform being integrally attached to said second end of the keeper strap; a substantially flat interchangeable cap having an upper side and a lower side, said lower side of said cap having female attachment means complementary to said male attachment means of the mounting platform; wherein said male attachment means and said female attachment means permit said cap to be removably attached to said mounting platform.

* * * * *